(12) United States Patent
Nolen et al.

(10) Patent No.: US 6,362,235 B1
(45) Date of Patent: Mar. 26, 2002

(54) METHOD, APPARATUS AND COMPOSITIONS FOR INHIBITING THE HUMAN SCENT TRACKING ABILITY OF MOSQUITOES IN ENVIRONMENTALLY DEFINED THREE DIMENSIONAL SPACES

(75) Inventors: J. A. Nolen, West Greenwich, RI (US); Robert H. Bedoukian, West Redding; Robert E. Maloney, Bethel, both of CT (US); Daniel L. Kline, Gainesville, FL (US)

(73) Assignees: Biosensory, Inc., Williamton; Bedoukian Research Inc., Danbury, both of CT (US); The United States of America as represented by the Secretary of Agriculture, Washington, DC (US)

( * ) Notice: Subject to any disclaimer, the term of this patent is extended or adjusted under 35 U.S.C. 154(b) by 0 days.

(21) Appl. No.: 09/307,907

(22) Filed: May 10, 1999

(51) Int. Cl.⁷ .................. A01N 31/00; A61K 31/045
(52) U.S. Cl. ............................................. 514/739
(58) Field of Search ......................... 514/760, 739

(56) References Cited

U.S. PATENT DOCUMENTS

| | | | |
|---|---|---|---|
| 4,569,947 A | 2/1986 | Stockton et al. | 514/724 |
| 4,693,890 A | 9/1987 | Wilson et al. | 424/78 |
| 4,759,228 A | 7/1988 | Butler et al. | 73/866 |
| 4,764,367 A | 8/1988 | Wilson et al. | 424/84 |
| 4,774,082 A | 9/1988 | Flashinski et al. | 424/78 |
| 4,933,371 A | 6/1990 | Hink et al. | 514/739 |
| 5,175,175 A | 12/1992 | Wilson et al. | 514/330 |
| 5,205,064 A | 4/1993 | Nolen | 43/112 |
| 5,250,575 A | 10/1993 | Wilson et al. | 514/739 |
| 5,587,401 A | 12/1996 | Vander Meer et al. | 514/675 |
| 5,648,390 A | 7/1997 | Vander Meer et al. | 514/558 |
| 5,662,914 A | 9/1997 | Shorey et al. | 424/405 |
| 5,665,344 A | 9/1997 | Pair et al. | 424/84 |
| 5,665,781 A | 9/1997 | Warren et al. | 514/703 |
| 5,721,274 A * | 2/1998 | Meer et al. | 514/532 |

FOREIGN PATENT DOCUMENTS

JP 04021606 * 12/1992

OTHER PUBLICATIONS

The Amer. Heritage Dic., 2nd Ed, pg. 113,816, 1982.*
Burton, Intrinsic mosquito repellency compounds, Amer. Prefum. Cosmet., vol. 84 No. 4, pp. 41–2,4, 1969.*

* cited by examiner

*Primary Examiner*—Alton Pryor
(74) *Attorney, Agent, or Firm*—George W. Rauchfuss, Jr.; Ohlandt, Greeley, Ruggiero & Perle, LLP

(57) ABSTRACT

The ability of mosquitoes to locate a target by olfactory emissions of the target is inhibited by dispensing into a spatial area an inhibiting effective amount of at least one inhibiting compound selected from the group consisting of 3-methyl-1-alkene-3-ols of the formula:

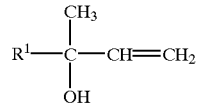

and 3-methyl-1-alkyn-3-ols of the formula:

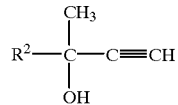

wherein $R^1$ and $R^2$ are each independently a saturated or unsaturated aliphatic hydrocarbon group containing from 1 to 12 carbon atoms.

37 Claims, No Drawings

METHOD, APPARATUS AND COMPOSITIONS FOR INHIBITING THE HUMAN SCENT TRACKING ABILITY OF MOSQUITOES IN ENVIRONMENTALLY DEFINED THREE DIMENSIONAL SPACES

FIELD OF THE INVENTION

This invention relates to a method, apparatus and compositions for inhibiting the ability of mosquitoes to locate or track a human body by scent detection. More particularly, the invention relates to the use of certain compounds in compositions and apparatus to inhibit mosquitoes' ability to detect humans by scent detection.

BACKGROUND

Compounds, compositions and formulations for protecting human beings from being bitten by mosquitoes are known in the art. Generally, these compounds, compositions and formulations are based on their ability to persist on the skin of the person upon topical or surface application for a time sufficient to repel mosquitoes. Numerous adjuvant materials have been added to mosquito repellants to increase the persistence of the repellents to the skin of a person. However, despite the various attempts to improve the repelling activity of the known mosquito repellents, these attempts have generally not been successful, as almost anyone who has used such mosquito repellents can attest.

Thus, the art has been searching for new and more effective repelaents against mosquitoes. However, the search for more effective mosquito repellents has not generally been met with success since most mosquito repellents have been found only to possess a limited degree of repellency and are generally not particularly effective. There is, therefore, a need for more effective means to deter mosquitoes from locating and biting humans and other targets such as livestock. Moreover, this need has recently become more acute and urgent because mosquitoes have been discovered to be carriers of significant diseases that can be passed on to a target by the mosquitoes biting the target. A further need is to be able to reduce the use of environmentally unfriendly pesticides.

SUMMARY OF THE INVENTION

The inventors have discovered that compounds, compositions and formulations heretofore proposed as repellents for mosquitoes have lacked the necessary efficacy due to the ability of mosquitoes to locate and be drawn to the targets by olfactory emissions of the target. Thus, if a mosquito enters a zone or space where a potential target is located, the mosquito can be attracted to the target by olfactory emissions of the target and, this olfactory attraction is sufficient to overcome any repellency activity of the repellent compound, composition or formulation applied on the target. Therefore, the present invention provides compositions and formulations containing compounds usable in methods and apparatus for inhibiting the olfactory target tracking abilities of mosquitoes when an effective amount of the inhibiting compound(s) is/are dispersed in a three dimensional atmospheric space.

According to this invention, the ability of mosquitoes to locate a target is inhibited by dispensing into a spatial area an inhibiting effective amount of at least one inhibiting compound selected from the group consisting of 3-methyl-1-alkene-3-ols of the formula:

$$R^1\text{—}\underset{\underset{OH}{|}}{\overset{\overset{CH_3}{|}}{C}}\text{—}CH\text{=}CH_2$$

and 3-methyl-1-alkyn-3-ols of the formula:

$$R^2\text{—}\underset{\underset{OH}{|}}{\overset{\overset{CH_3}{|}}{C}}\text{—}C\text{≡}CH$$

wherein $R^1$ and $R^2$ are each independently a saturated or unsaturated aliphatic hydrocarbon group containing from 1 to about 12 carbon atoms.

The inhibiting compound can be dispensed into the three dimensional atmospheric space by any suitable means sufficient to provide an inhibiting effective amount of the inhibiting compound(s). Such dispensing means includes, for example, evaporation, atomization and ionic dispersion of the inhibiting compound from any suitable composition or formulation. Such composition or formulation will generally comprise a base vehicle containing at least one of the inhibiting compounds.

DETAILED SUMMARY OF THE INVENTION

The inventors have discovered that if an effective amount of at least one inhibiting compound selected from the group consisting of 3-methyl-1-alkene-3-ols of the formula:

$$R^1\text{—}\underset{\underset{OH}{|}}{\overset{\overset{CH_3}{|}}{CH}}\text{—}CH\text{=}CH_2$$

and 3-methyl-1-alkyn-3-ols of the formula:

$$R^2\text{—}\underset{\underset{OH}{|}}{\overset{\overset{CH_3}{|}}{C}}\text{—}C\text{≡}CH$$

wherein $R^1$ and $R^2$ are each independently a saturated or unsaturated aliphatic hydrocarbon group containing from 1 to about 12 carbon atoms is dispensed into the atmosphere of a three dimensional environmental space, the ability of mosquitoes to locate and track a target, such as humans or livestock, by the target's olfactory emissions is inhibited.

Any suitable 3-methyl-1-alkene-3-ols or 3-methyl-1-alkyn-3-ol of the formulas may be employed in the method, compositions and apparatus of this invention. Especially suitable inhibiting compounds are nerolidol, 3-methyl-1-octen-3-ol, linalool and dehydrolinalool. Depending on the particular mosquito species, either the 3-methyl-1-alkyn-3-ols or the 3-methyl-1-alkene-3-ols are better inhibitors than the other class of components and will be preferred for that species of mosquito. The inhibiting compounds may be utilized singly or as mixtures of two or more of such compounds.

Any suitable inhibiting effective amount of the inhibiting compound(s) may be employed. Such inhibiting effective amounts can include amounts, based on the square footage of land or base surface area of the environmental area to be treated, within the range of from about 0.000005 g/hr/ft² to about 0.004 g/hr/ft², preferably amounts within the range of from about 0.00015 g/hr/ft² to about 0.0002 g/hr/ft², and especially an amount of about 0.00016 g/hr/ft².

The inhibiting compounds for use in this invention may be provided in an essentially pure form of the inhibiting compounds or as a component of a natural essential oil having a concentration of an inhibiting compound sufficient to make it practical and feasible to dispense an inhibiting effective amount of inhibiting compound. Generally, the essential oil will contain a concentration of the inhibiting compound of at least about 2%, preferably at least about 5%, and especially at least about 50% by weight. For example, the inhibiting compound can be provided as a synthetically produced, essentially pure compound or as a component of an essential oil such as basil oil, ho wood oil and the like.

The inhibiting compounds of this invention, or essential oils containing such inhibiting compounds, may be employed in any formulation suitable for dispensing inhibiting effective amounts of the compounds. The compounds will generally be employed in formulations comprising a suitable vehicle containing the inhibiting compounds. For example, the inhibiting compound can be formulated in a specially formulated wax-like medium or vehicle engineered to release desired amounts of vaporous inhibiting compound at ambient temperatures, such as those mediums or vehicles available from Koster Keunen of Watertown, Conn. An example of such a wax-like medium available from Koster Keunen is known as Insect Repellent Wax Bar No. 9, which is a blend of waxes having the following general composition: fatty acids ranging in carbon chain length of from $C_{16}$ to $C_{22}$, fatty alcohols ranging in carbon chain length of from $C_{16}$ to $C_{22}$, paraffinic hydrocarbons ranging in carbon chain length of from $C_{19}$ to $C_{47}$, branched hydrocarbons ranging in carbon chain length of from $C_{23}$ to $C_{69}$, beeswax and other natural waxes such as candelilla and carnauba. The wax mixture will generally be formulated with concentrations of the inhibiting compounds of this invention ranging from about 20% to 60% and the formulation has a congealing point which may vary from about 75° C. to about 45° C. Alternatively, the inhibiting compound can be formulated in a porous medium or vehicle suitable for releasing effective amounts of the inhibiting compound. As an example of such porous medium or vehicle is a polyester membrane material having micropores encasing a block of inhibiting compound saturated fibers that gradually releases the inhibiting compound so that it permeates the microporous membrane and is released to the environment. Such porous membrane known as World of Fragrance™ cups is available from Waterbury Companies, Inc. of Waterbury, Conn.

The formulations can be placed in any suitable container or device for dispensing the inhibiting compound. For example, the formulations can be placed in a suitable fan-equipped device so that one can obtain, for example, fan-driven evaporation of the inhibiting compound from a porous medium or wax-like medium containing the inhibiting compound. As examples of such fan-equipped devices, there can be mentioned the devices disclosed in U.S. Pat. No. 5,370,829 of Waterbury Companies, Inc. and the apparatus disclosed in U.S. Pat. No. 5,799,436 of Biosensory Insect Control Corporation, each of said patents being incorporated herein by reference thereto.

Another suitable means of dispensing the inhibiting compound is by atomization and/or ionic dispersion of the compound as suitable-sized, positively-charged droplets from a suitable atomization or ionic dispersing apparatus, such as the Ionic Wind™ device, available from Brandenburg, Ltd. of Brierery Hill, United Kingdom.

The inhibiting compounds of this invention are effective against mosquitoes, such as for example, *Aedes taeniorhyncus* (Black Salt Marsh mosquito), *Culex nigripalpus, Aedes aegypti, Aedes albpictus* (Asian Tiger mosquito), *Culex pipiens* (common house mosquito) and the like.

The use of this invention is illustrated by the following non-limited examples.

EXAMPLE 1

A triple cage, dual-port olfactometer, illustrated and described in detail by Posey et al. J. Med. Entomol. 35(3), 330–334 (1998), was used to study the responses of 6 to 8 day old, laboratory-reared adult female *Aedes aegypti* mosquitoes. This system allows mosquitoes to choose between two different stimuli. The olfactometer is constructed of clear acrylic, comprises three test chambers in a tiered configuration, has paired removable sleeves, and mosquito traps on each chamber, and is equipped with a filtered external air supply system that allows precise temperature (+/−0.5° C.) and relative humidity (+/−2%) control. Only one chamber at a time was used for the tests. Outside air was conditioned prior to entry through the choice ports, the mosquito trap, and the olfactometer by passing through a series of charcoal filters and then heated and humidified, if necessary.

One hour before initiation of tests, about 75 female *Ae. aegypti* mosquitoes were aspirated into the olfactometer chamber and allowed to acclimatize for that one hour before testing. Test compounds were placed into test ports upwind of the traps and olfactometer chamber. A completely randomized design was used for cage position.

Competitive tests were conducted. In these competitive tests, the inhibiting compound was placed into one of the ports (treatment port); the second port (check port) had the same apparatus but no chemical inhibiting compound. In these tests, inhibiting compounds were presented in glass Pyrex petri dishes (60×15 mm) that had been cleaned and sterilized in a vacuum oven and then handled only with gloves to minimize any chance of contamination and placed into one port (Treatment Port) along with another petri dish containing 500 μL of Clara Sludge (CS), a synthetic human attractant. The other port (Check Port) contained an untreated petri with no inhibiting compound and a second petri dish containing 500 μL CS. Various concentrations (25, 100, 250, 500 and 1000 μL) of the compounds were used in these tests. Each test was conducted for a period of 3 minutes; the number of mosquitoes trapped in the baited ports, and those remaining in the cage, were counted. The data are then presented as a percentage of total mosquitoes in the cage that were attracted to each port and the percentage of mosquitoes remaining in the cage (i.e., not attracted to either port).

Results of the competitive tests are set forth in the following Table 1.

TABLE 1

Competitive Tests

% Mosquitoes Entering

| Test Compound and Amount | Treatment Port (Inhibitor Port) | Control Port (Human Scent Port) | % Mosquitoes Remaining in Cage |
|---|---|---|---|
| Dehydrolinalool 25 micro liter | 30.23 | 50.77 | 19 |
| Dehydrolinalool 100 micro liter | 31.13 | 53.87 | 15 |
| Dehydrolinalool 250 micro liter | 22.6 | 44.6 | 32.8 |
| Dehydrolinalool 500 micro liter | 24.8 | 56.47 | 24.18 |
| Dehydrolinalool 1000 micro liter | 26.11 | 42.76 | 27.12 |
| Linalool 25 micro liter | 21.98 | 56.89 | 21.14 |
| Linalool 100 micro liter | 31.3 | 45.61 | 23.08 |
| Linalool 250 micro liter | 16.57 | 47.3 | 36.13 |
| Linalool 500 micro liter | 16.13 | 44.56 | 39.31 |
| Linalool 1000 micro liter | 27.24 | 44.14 | 31.3 |

For comparison purposes, 500 µL of the human scent (CS) was also placed alone in the Treatment Port, and with only an empty petri dish in the Check Port. The Treatment Port with the CS attracted 69 to 65% of the mosquitoes, with 30 to 35% of the mosquitoes remaining in the cage, and none being attracted to the Check Port with only the petri dish. At all tested concentration levels, linalool and dehydrolinalool are shown to greatly inhibit the ability of mosquitoes to locate the human scent (CS) as shown by the much lower percentage of mosquitoes captured in the Treatment Port compared to the Human Scent Port.

EXAMPLE 2

Tests identical to that described in Example 1 were conducted with test compounds when employed together with the synthetic human attractant (CS) in a port. The test combinations were:

(1) CS vs. CS (comparison)
(2) dehydrolinalool+CS vs. CS
(3) linalool+CS vs. CS

Also for comparison purposes, a known topical mosquito repellant, Deet, namely N,N-diethyl-3-methylbenzamide, was employed to compare to linalool and to dehydrolinalool. Each test compound was tested at 100, 250 and 500 µL. The results are presented in Tables 2, 3 and 4. The results are again presented as percent mosquitoes attracted to Ports 1 or 2 or not attracted to either port.

TABLE 2

(100 micro liter treatments)

| Test Compound and Amount | % Mosquitoes Entering Port 1 | Port 2 | % Mosquitoes Remaining in Cage |
|---|---|---|---|
| 1 Human scent vs. 2 human scent | 50.5 | 44 | 5.5 |
| 1 Dehydrolinalool vs. 2 human scent | 18.1 | 63 | 18.9 |
| 1 Linalool vs. 2 human scent | 22.5 | 50.7 | 26.8 |

TABLE 2-continued (100 micro liter treatments)

| Test Compound and Amount | % Mosquitoes Entering Port 1 | Port 2 | % Mosquitoes Remaining in Cage |
|---|---|---|---|
| 1 Deet vs. 2 dehydrolinalool | 60.1 | 20.1 | 19.8 |
| 1 Deet vs. 2 linalool | 56.3 | 17.5 | 26.2 |

TABLE 3

(250 micro liter treatments)

| Test Compound and Amount | % Mosquitoes Entering Port 1 | Port 2 | % Mosquitoes Remaining in Cage |
|---|---|---|---|
| 1 Human scent vs. 2 human scent | 49.9 | 39.4 | 8.7 |
| 1 Dehydrolinalool vs. 2 human scent | 20.1 | 59.2 | 20.6 |
| 1 Linalool vs. 2 human scent | 14.9 | 56.8 | 28.4 |
| 1 Deet vs. 2 dehydrolinalool | 48.8 | 22.5 | 29.2 |
| 1 Deet vs. 2 linalool | 48.1 | 25.7 | 26.2 |

TABLE 4

(500 micro liter treatments)

| Test Compound and Amount | % Mosquitoes Entering Port 1 | Port 2 | % Mosquitoes Remaining in Cage |
|---|---|---|---|
| 1 Human scent vs. 2 human scent | 47.3 | 46.8 | 5.9 |
| 1 Dehydrolinaldol vs. 2 human scent | 20.6 | 55.5 | 23.9 |
| 1 Linalool vs. 2 human scent | 25.7 | 55.6 | 15.7 |
| 1 Deet vs. 2 dehydrolinalool | 42.1 | 30.3 | 27.6 |
| 1 Deet vs. 2 linalool | 49.5 | 23.1 | 27.3 |

EXAMPLE 3

In a further test of the inhibiting ability of the compounds of this invention, the following field test was conducted using linalool as the inhibiting compound. The study was conducted on a site adjacent to a wooded wetland breeding area in Sarasota, Fla. A trap baited with 200 ml/min $CO_2$, equivalent to the respiration of a 91 kg (200 lb) man, ran continuously each night as an experimental control. The trap collections were first used to count the mosquito population and were then examine to identify the species present. The mosquito population was about 91% *Culex nigripalpus*, the St. Louis encephalitis vector in Florida.

The experimental design was a 2×2 Latin Square. Tests were conducted in two open areas 24 meters (80 feet) apart labeled Locations 1 and 2. Each area was 2.4 meters×2.4 meters (8 ft×8 ft), i.e., 5.76 m² (64 ft²). Wooden poles 1.38 meters (4.5 feet) high and having inhibiting compound dispensers thereon were driven into the ground at the corners of the square area. On alternate nights, one area was unprotected by inhibiting compound while the other area had inhibiting compound dispensed from the dispenser. In operation, the dispenser emitted linalool inhibitor having 95% active ingredient at a rate of 20 mg/hr to 40 mg/hr.

Landing counts were taken from the arms, legs and torso of a test subject known to be moderately attractive to mosquitoes who was seated in the center of the square area. At 15-minute intervals over a period of 2 to 3 hours during peak mosquito activity, the subject changed his position, alternating between Locations 1 and 2. If there was no activity for five minutes, the test subject walked around the inside perimeter of the square area in an attempt to draw attention to his presence. Mosquitoes were killed to prevent double counting.

The mosquitoes were observed to exhibit a behavior similar to swarming each evening around 6:45 to 7:00 PM. On some cue, they emerge en masse from the wooded wetland and fan out in a radial direction foraging for blood hosts. The period of peak activity is evidenced by a sharp increase in landing counts followed by a sharp decrease as the wave of outbound mosquitoes passes the test location. This behavior introduces two variables that must be taken into account. The first affects the experimental design and the second affects the interpretation of the results.

To be most accurate, an experimental trial must span a period before and after peak activity. Ending a trial at or near the time of peak activity, for example, will result in a larger landing count for the treatment used last, skewing the result. The starting time and duration of trials were adjusted to avoid distorting the landing counts.

It is also recognized that the landing counts represent both:

1. mosquitoes drawn to the human subject by his scent, and
2. mosquitoes that encounter the human subject because he is in their line of flight as they leave the water.

If the inhibitor impairs the mosquitoes' scent-tracking ability, it will affect the former but not the latter. This fact must be taken into account when interpreting the results.

The sites selected represent a worse case condition that is experienced only by those located adjacent to a breeding site and in the line of flight as the mosquitoes come off the water. For a measure of performance more typical of the average homeowner, a test was conducted from 7:00 AM to 9:00 AM in the morning when activity is not at its peak.

Linalool reduced the mosquito landing counts by an average of 53% over the three trials. The unprotected human subject experienced 286 landings compared to 135 landings when surrounded by linalool dispensed from the dispensers.

The range for individual trials is a reduction of landings by 36% to 68% during periods of peak activity and by 73% in the morning trial when mosquito activity was light.

These results indicate linalool's ability to reduce the landing counts of *Culex nigripalpus* on humans in open areas by inhibiting the mosquitoes' ability to track the human's olfactory emissions.

With the foregoing description of the invention, those skilled in the art will appreciate that modifications may be made to the invention without departing from the spirit thereof. Therefore, it is not intended that the scope of the invention be limited to the specific embodiments illustrated and described.

We claim:

1. A method of inhibiting the ability of mosquitoes to sense a target by olfactory sensing of the target within a three dimensional environmental space having a land or base surface area, the method comprising dispensing into the atmosphere of the three dimensional environmental space an inhibiting effective amount of at least one inhibiting compound to inhibit the ability of mosquitoes to sense a target, wherein said at least one inhibiting compound is selected from the group consisting of 3-methyl-1-alkene-3-ols of the formula:

and 3-methyl-1-alkyn-3-ols of the formula:

wherein $R^1$ and $R^2$ are each independently a saturated or unsaturated aliphatic hydrocarbon group containing from 1 to about 12 carbon atoms.

2. The method according to claim 1, wherein the inhibiting effective amount ranges from about 0.000005 g/hr/$ft^2$ to about 0.0004 g/hr/$ft^2$ based on the square footage of the land or base surface area of the environmental space.

3. The method according to claim 1, wherein the inhibiting effective amount ranges from about 0.00015 g/hr/ft2 to about 0.0002 g/hr/$ft^2$ based on the square footage of the land or base surface area of the environmental space.

4. The method according to claim 1, wherein the at least one inhibiting compound is selected from nerolidol, 3-methyl-1-octen-3-ol and dehydrolinalool.

5. The method according to claim 1, wherein the at least one inhibiting compound comprises dehydrolinalool.

6. The method according to claim 1, wherein the dispensing of the at least one inhibiting compound comprises dispensing by a method selected from volatilization, evaporation, atomization and ionic dispersion of the at least one inhibiting compound from a formulation comprising a vehicle containing the at least one inhibiting compound.

7. The method according to claim 6, wherein the dispensing comprises fan-driven evaporation of the at least one inhibiting compound from a formulation in which the vehicle is a porous medium.

8. The method according to claim 6, wherein the dispensing comprises fan-driven evaporation of the at least one inhibiting compound from a formulation in which the vehicle is a waxy solution.

9. The method according to claim 6, wherein the dispensing comprises atomization of the at least one inhibiting compound from the formulation.

10. The method according to claim 6, wherein the dispensing comprises ionic dispersion of the at least one inhibiting compound from the formulation.

11. The method according to claim 5, wherein the dehydrolinalool is dispensed by fan-driven evaporation of dehydrolinalool from a formulation of a porous medium containing dehydrolinalool.

12. The method according to claim 5, wherein the dehydrolinalool is dispensed by fan-driven evaporation of dehydrolinalool from a formulation of a waxy solution containing dehydrolinalool.

13. The method according to claim 5, wherein the dehydrolinalool is dispensed by atomization of dehydrolinalool from a base composition.

14. The method according to claim 5, wherein the dehydrolinalool is dispersed by ionic dispersion of dehydrolinalool from a formulation of a vehicle and dehydrolinalool.

15. A method of inhibiting the ability of mosquitoes to sense a target by olfactory sensing of the target within a three dimensional environmental space having a land or base surface area, the method comprising dispensing into the, atmosphere of the three dimensional environmental space an inhibiting effective amount of at least one inhibiting compound to inhibit the ability of mosquitoes to sense a target, wherein said at least one inhibiting compound is selected from the group consisting of 3-methyl-1-alkene-3-ols of the formula:

$$R^1-\underset{\underset{OH}{|}}{\overset{\overset{CH_3}{|}}{C}}-CH=CH_2$$

and 3-methyl-1-alkyn-3-ols of the formula:

$$R^2-\underset{\underset{OH}{|}}{\overset{\overset{CH_3}{|}}{C}}-C\equiv CH$$

wherein $R^1$ and $R^2$ are each independently a saturated or unsaturated aliphaltic hydrocarbon group containing from 1 to about 12 carbon atoms, and the dispensing into the atmosphere is by a method selected from fan-driven evaporation, volatilization, atomization or ionic dispersion.

16. The method according to claim 12, wherein the at least one inhibiting compound comprises linalool.

17. The method according to claim 16, wherein the linalool is dispensed by fan-driven evaporation of linalool from a formulation of a porous medium containing linalool.

18. The method according to claim 16, wherein the linalool is dispensed by fan-driven evaporation of linalool from a formulation of a waxy solution containing linalool.

19. The method according to claim 16, wherein the linalool is dispensed by atomization of linalool from a formulation of a vehicle and linalool.

20. The method according to claim 16, wherein the linalool is dispersed by ionic dispersion of linalool from a formulation of a vehicle and linalool.

21. The method according to claim 15, wherein the composition is sufficient to provide an inhibiting effective amount of the at least one inhibiting compound ranging from about 0.00015 g/hr/ft2 to about 0.0002 g/hr/ft$^2$ per square footage of the land or base surface area of the three dimensional environmental space.

22. The method according to claim 15, wherein the at least one inhibiting compound is selected from nerolidol, 3-methyl-1-octen-3-ol, linalool and dehydrolinalool.

23. The method according to claim 15, wherein the at least one inhibiting compound comprises linalool.

24. The method according to claim 15, wherein the at least one inhibiting compound comprises dehydrolinalool.

25. The method according to claim 15, wherein the method is able to dispense the at least one inhibiting compound by a method selected from volatilization, evaporation, atomization and ionic dispersion of the at least one inhibiting compound.

26. The method according to claim 15, wherein a composition is dispensable by fan-driven evaporation of the at least one inhibiting compound and a vehicle is a porous medium.

27. The method according to claim 15, wherein a composition is dispensable by fan-driven evaporation of the at least one inhibiting compound and a vehicle is waxy solution.

28. The method according to claim 25, wherein a composition is dispensable by atomization of the at least one inhibiting compound.

29. The method according to claim 25, wherein a composition is dispensable by ionic dispersion of the at least one inhibiting compound.

30. The method according to claim 23, wherein the linalool is dispensable by fan-driven evaporation of linalool and a vehicle is of a porous medium containing linalool.

31. The method according to claim 23, wherein the linalool is dispensable by fan-driven evaporation of linalool and a vehicle is of a waxy solution containing linalool.

32. The method according to claim 23, wherein the linalool is dispensable by atomization of linalool.

33. The method according to claim 23, wherein the linalool is dispersible by ionic dispersion of linalool.

34. The method according to claim 24, wherein the dehydrolinalool is dispensable by fan-driven evaporation of dehydrolinalool and a vehicle is of a porous medium containing dehydrolinalool.

35. The method according to claim 24, wherein the dehydrolinalool is dispensable by fan-driven evaporation of dehydrolinalool and a vehicle is of a waxy solution containing dehydrolinalool.

36. The method according to claim 24, wherein the dehydrolinalool is dispensable by atomization of dehydrolinalool.

37. The method according to claim 24, wherein the dehydrolinalool is dispersible by ionic dispersion of dehydrolinalool.

* * * * *